United States Patent
Chen

(10) Patent No.: US 7,003,122 B2
(45) Date of Patent: Feb. 21, 2006

(54) PORTABLE AUDIO DEVICE WITH BODY/MOTION SIGNAL REPORTING DEVICE

(76) Inventor: Yu-Yu Chen, 2Fl., No. 349, Wushing St., Shinyi Chiu, Taipei (TW) 110

( * ) Notice: Subject to any disclaimer, the term of this patent is extended or adjusted under 35 U.S.C. 154(b) by 67 days.

(21) Appl. No.: 10/733,324

(22) Filed: Dec. 12, 2003

(65) Prior Publication Data

US 2005/0129253 A1  Jun. 16, 2005

(51) Int. Cl.
*A61B 7/04* (2006.01)
*A61B 5/04* (2006.01)
*H04B 3/00* (2006.01)
*A63B 71/00* (2006.01)

(52) U.S. Cl. ............... 381/67; 600/500; 482/8; 482/9; 381/77

(58) Field of Classification Search ........... 381/67; 600/528–529
See application file for complete search history.

(56) References Cited

U.S. PATENT DOCUMENTS

| 5,314,389 | A | * | 5/1994 | Dotan ................... 482/3 |
| 5,976,083 | A | * | 11/1999 | Richardson et al. ....... 600/300 |
| 6,080,110 | A | * | 6/2000 | Thorgersen ............... 600/500 |
| 6,572,511 | B1 | * | 6/2003 | Volpe ................... 482/4 |
| 6,607,493 | B1 | * | 8/2003 | Song .................... 600/502 |
| 6,793,607 | B1 | * | 9/2004 | Neil .................... 482/8 |

* cited by examiner

*Primary Examiner*—Laura A. Grier
(74) *Attorney, Agent, or Firm*—Rosenberg, Klein & Lee

(57) ABSTRACT

A portable audio device includes an audio signal generating device for generating an audio signal, a body/motion signal detecting device for detecting and generating a body/motion signal, a signal loop selecting circuit which is coupled to the body/motion signal detecting device, a timer control circuit which generates a loop selection controlling signal at a predetermined time interval, a control device and an audio signal output device which outputs the audio signal vocally. The audio signal generated by the audio signal output device is transmitted to the audio signal output device, and the body signal is transmitted to the audio signal output device under control of the loop selection controlling signal generated by the timer control circuit at the predetermined time interval.

4 Claims, 2 Drawing Sheets

PORTABLE AUDIO DEVICE WITH BODY/MOTION SIGNAL REPORTING DEVICE

BACKGROUND OF THE INVENTION

1. Field of the Invention

The present invention relates to a wireless audio device, and more particularly to a portable audio device capable of playing audio signal and wirelessly receiving and reporting a body/motion signal of a user.

2. Description of the Prior Art

In the modern society, people have been working busily for most of the time. To relax themselves from heavy work pressure, most of them enjoy music or do exercises. Commercially, there are various entertaining equipment to provide amusing entertainment. Among these, portable audio devices like radio, CD Walkman and MP3 are mostly popular, that are convenient to use at anywhere.

Moreover, there are many exercisers for people who require appropriate exercises. For a person to accurately control a moderate quantity of exercise and monitor personal physical condition, various types of body/motion signal sensing devices have been researched and developed, e.g. pedometer, jog-speed sensing device, bicycle-speed sensing device, heartbeat sensing device and so on.

Most conventional body signal sensing devices or motion signal sensing devices are designed to provide one single detecting and sensing function. That is, each type of conventional sensing device is able to detect and sense only one type of signal at a time. For example, there are various heartbeat sensing devices commercially available. In U.S. Pat. No. 5,491,474, a telemetric transmitter unit is disclosed. The transmitter electronics is coupled to each electrode by means of a conductive plastic layer for transmission of signal. In U.S. Pat. No. 4,513,753, a heartbeat rate indicator in the form of wristwatch is disclosed. Moreover, U.S. Pat. No. 5,622,180 describes a device for measuring heartbeat rate that includes a wrist strap with skin contact electrodes and a coil receiver for receiving telemetrically transmitted heartbeat signals either from a wireless receiver or from the skin contact electrodes.

Also, there are many types of pedometers in the market. For example, U.S. Pat. Nos. 4,371,945 and 5,164,967 disclose a pedometer for calculating a distance which a user walks, jogs or runs by electronically measuring the length of each stride taken by the use.

All of the aforesaid conventional body signal sensing devices and motion signal sensing devices are designed to have only one detecting and sensing function. That is, in practical use of these conventional sensing devices, they can detect and display only one type of signal. In fact, those products do not match the users' requirements. Some producers have devoted to develop a few body signal sensing devices with multiple functions. Take for an example. U.S. Pat. No. 5,891,042 discloses a fitness monitoring device that includes an electronic pedometer which responds to a user's body motion at each step and a wireless heart rate monitor which is wirelessly coupled to the electronic pedometer. The pedometer is fitted to the user's waist and the wireless heart rate monitor is fitted to the user's chest. The heartbeat signal is transmitted wirelessly to and is displayed on the pedometer. Practically, it is not easy and inconvenient for the user to view the data displayed on the pedometer.

Also, an electronic combined pulse meter and pedometer is taught in U.S. Pat. No. 5,475,725, in which a single sensor is used for determining the walking pace and pulse rate, and the data are displayed on the pedometer. In U.S. Pat. No. 6,302,789, a new pedometer with game mode is disclosed, which can be used as a game by a child to get some exercise such as walking and/or running without reluctance.

U.S. Pat. No. 5,314,389 discloses an exercise monitor which provides an exercising person information at any desired period of time about his pulse rate at that instant. The pulse rate is transmitted to the earphones by wire at predetermined intervals when the music is still playing. However, the motion of the user is hindered and restricted by the connecting wire between the ECG apparatus and the earphones. Also, the exercise monitor is capable to provide pulse rate information only.

It is noted that there is no appropriate body/motion signal sensing device which can detect body/motion signal and provide audio signal reporting function.

SUMMARY OF THE INVENTION

Thus, a primary object of the invention is to provide a portable audio device with body/motion signal reporting device which is capable to provide audio and body/motion signal information in a single device.

Another object of the invention is to provide a portable audio device with body/motion signal reporting device. The portable audio device includes a heartbeat detector and a pace detector that are capable to detect a heartbeat signal and a pace signal of a user. By means of the portable audio device, when the user takes exercise, he can listen to music and monitor his heartbeat signal and pace signal at the same time. With the multiple functions provided by the portable audio device, the user can save a lot of money and reduce the loading of using separate devices including heartbeat sensing device, pedometer and Walkman.

To achieve the above and other objects, in accordance with the present invention, there is provided with a portable audio device with body/motion signal reporting device. The portable audio device comprises an audio signal generating device for generating an audio signal, a body/motion signal detecting device for detecting and generating a body/motion signal, a signal loop selecting circuit which is coupled to the body/motion signal detecting device, a timer control circuit which generates a loop selection controlling signal at predetermined time intervals, a control device and an audio signal output device which outputs the audio signal vocally. The audio signal generating device transmits the audio signal to the audio signal output device. When the audio signal output device outputs the audio signal, at predetermined time intervals, the loop selection controlling signal from the timer control circuit drives the signal loop selecting circuit to transmit the body/motion signal to the audio signal output device which reports the user's body/motion signal data. In a preferred embodiment, the body signal detecting device comprises a heartbeat signal detecting device and the motion signal detecting device comprises a pedometer.

BRIEF DESCRIPTION OF THE DRAWINGS

The present invention will be apparent to those skilled in the art by reading the following description of the best mode and a preferred embodiment of a device for carrying out the present invention, with reference to the attached drawings, in which.

DETAILED DESCRIPTION OF THE PREFERRED EMBODIMENT

Figure 1:
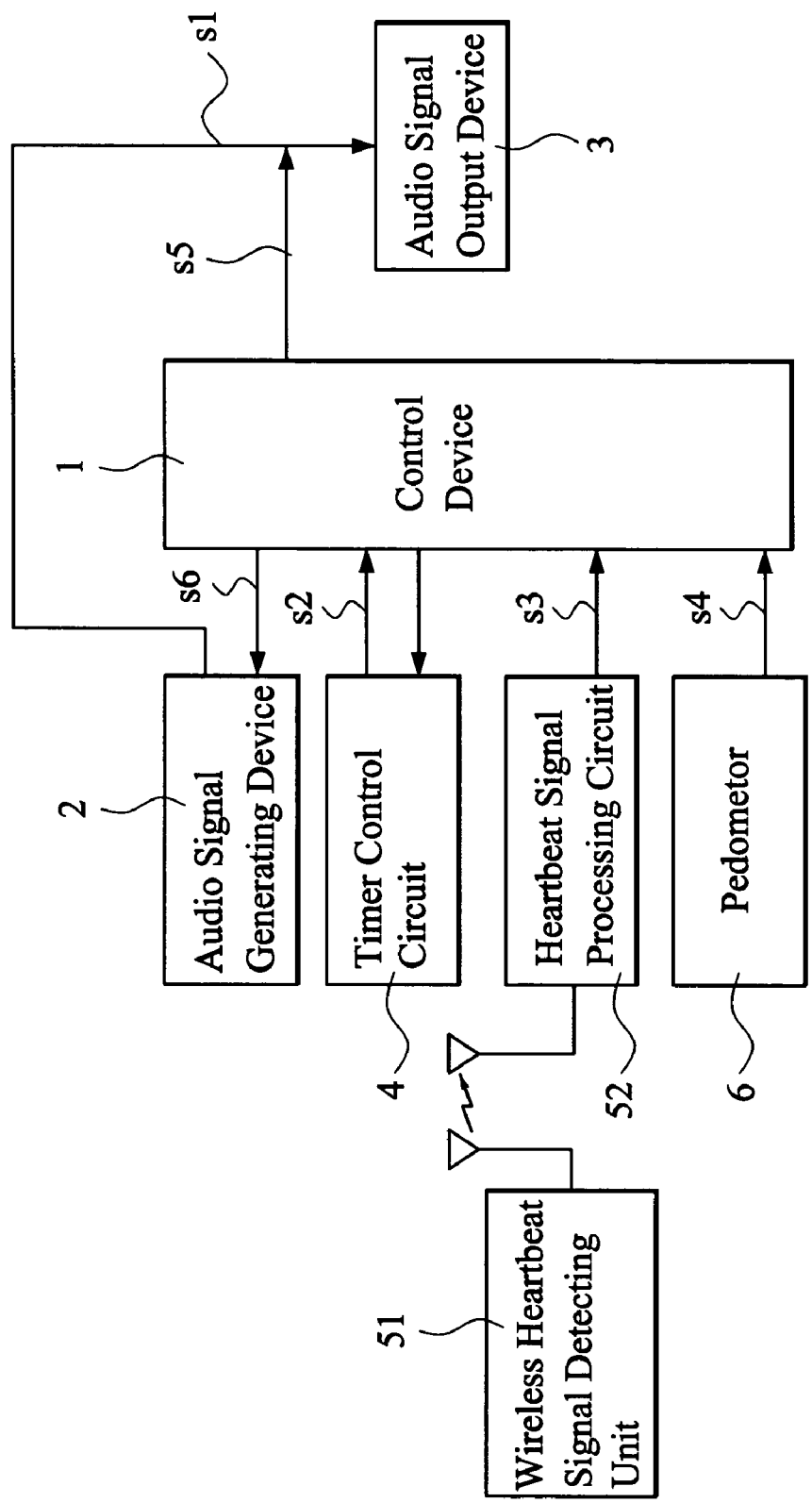
FIG. 1 is a functional block diagram of a portable audio device with body/motion signal reporting device constructed in accordance with the present invention.

With reference to the drawings and in particular to FIG. 1 which is a functional block diagram of a portable audio device with body/motion signal reporting device constructed in accordance with the present invention, the portable audio device comprises a control device 1 which is in connection with an audio signal generating device 2. The audio signal generating device 2 is capable of generating and providing an audio signal s1 which is transmitted to an audio signal output device 3 under the control of the control device 1. Moreover, the portable audio device comprises a timer control circuit 4 which is connected to the control device 1. The timer control circuit 4 controls the playing time of the audio signal.

The portable audio device also comprises a wireless heartbeat sensing device including a wireless heartbeat signal detecting unit 51 and a heartbeat signal processing circuit 52 which is connected to the control device 1. The wireless heartbeat signal detecting unit 51 detects a series of heartbeat signals of a user and transmits the detected heartbeat signal to the heartbeat signal processing circuit 52 by means of wireless signal transmission approach. Under control of the control device 1 and the timer control circuit 4, the heartbeat signal s3 from the heartbeat signal processing circuit 52 is transmitted to the audio signal output device 3 which vocally reports the user's heartbeat data at a predetermined time interval.

The portable audio device also comprises a pedometer 6 which is connected to the control device 1. The pedometer 6 detects and calculates an accumulated number of paces of walking, jogging or jumping taken by the user and generates a motion signal s4 to the control device 1. Under the control of the control device 1 and the timer control circuit 4, the motion signal s4 is transmitted to the audio signal output device 3 to vocally report the user's motion signal data at walking, jogging or jumping at predetermined time intervals.

Figure 2:
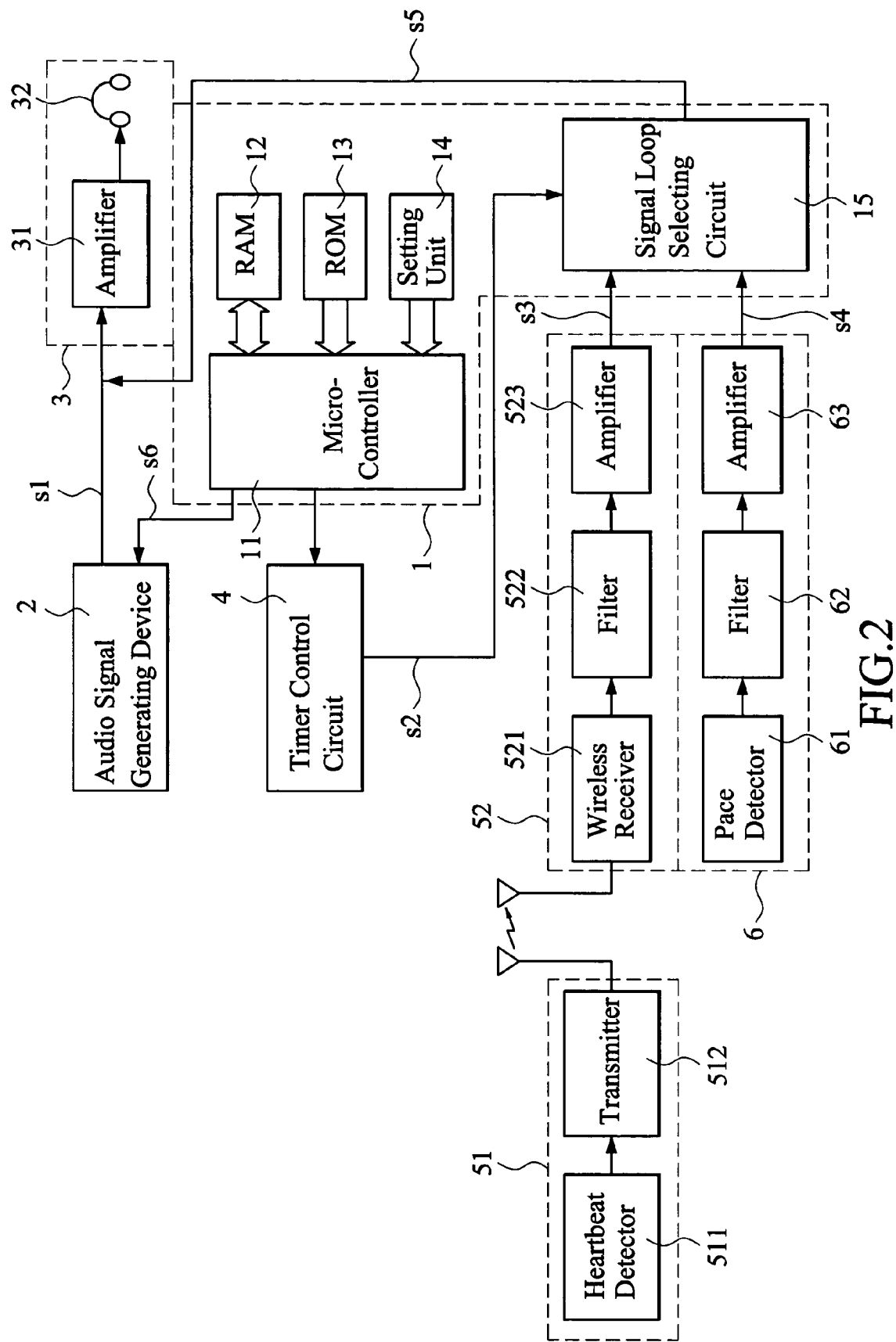
FIG. 2 is a block diagram showing a circuitry of the portable audio device with body/motion signal reporting device according to a preferred embodiment of the present invention.

Please refer to FIG. 2 which is a block diagram of the circuitry of the portable audio device in accordance with a preferred embodiment of the present invention. The control device 1 comprises a micro-processor 11, a random access memory (RAM) 12 for storing a data temporarily, a read only memory (ROM) 13 for storing an operating program and a setting unit 14 which comprises a plurality of buttons for setting of various parameters e.g. time.

The audio signal generating device 2 generates and transmits the audio signal s1 to the audio signal output device 3 which comprises an amplifier 31 and a sound producing device 32. The amplifier 31 amplifies the audio signal s1 and the sound producing device 32 converts the audio signal s1 into sound. The sound producing device 32 may comprise earphones. The audio signal generating device 2 may comprise a portable audio device (Walkman), CD player or any audio device that is capable of playing audio or compressed digital audio file like MP3.

The control device 1 further comprises a signal loop selecting circuit 15 which includes at least two signal transmission loops. The signal loop selecting circuit 15 is controlled by a loop selection controlling signal s2 generated by the timer control circuit 4.

The wireless heartbeat signal detecting unit 51 comprises a heartbeat detector 511 and a transmitter 512. The heartbeat detector 511 may comprise a conventional heartbeat detector that is worn around a chest of the user. The heartbeat signal detected by the heartbeat detector 511 is transmitted out wirelessly by the transmitter 512.

The heartbeat signal processing circuit 52 comprises a wireless receiver 521 for receiving the heartbeat signal transmitted from the transmitter 512 of the wireless heartbeat signal detecting unit 51. The heartbeat signal s3 is transmitted to a filter 522 for filtering the noise and then to an amplifier 523 for amplifying the heartbeat signal s3. The heartbeat signal s3 is forwarded to an input terminal of a first signal loop of the signal loop selecting circuit 15.

Moreover, the pedometer 6 comprises a pace detector 61, a filter 62 and an amplifier 63. The pace detector 61 may comprise a conventional pace detector that detects and transmits a pace signal s4 to the filter 62 for filtering the noise and then to the amplifier 63 for amplifying the pace signal s4. The pace signal s4 is then forwarded to an input terminal of a second loop of the signal loop selecting circuit 15.

The signal loop selecting circuit 15 is controlled by the loop selection controlling signal s2 generated by the timer control circuit 4 and selectively transmits the heartbeat signal s3 or the pace signal s4 or the two signals in sequence via an output terminal to the audio signal output device 3.

Accordingly, when the user performs exercise, he can listen to music from the audio signal output device 3. Meanwhile, he is vocally informed of his body signal s3 or motion signal s4 at predetermined time intervals according to the setting of the timer control circuit 4. Thereby, the user is able to monitor his physical status and listen to music during exercising.

At the reporting of the body signal s3 or motion signal s4, the music from the audio signal generating device 2 is simultaneously and continuously played. Alternatively, the audio signal s1 may be driven to pause by an audio control signal s6 from the micro-processor 11, and replay after the reporting of the body/motion signal.

In the preferred embodiment, the portable audio device is capable to report the heartbeat signal and pace signal of the user. Of course, the portable audio device can also be used for informing the user of his jog speed, walking distance and so on. Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A portable audio device with a body/motion signal reporting device for reporting at least one body/motion signal of a user, comprising:

an audio signal generating device for generating an audio signal;

an audio signal output device for receiving and outputting the audio signal from the audio signal generating device;

a timer control circuit for generating a loop selection controlling signal at a predetermined time interval;

a micro-processor for controlling the timer control circuit;

at least one body signal sensing device for detecting and transmitting at least one body signal of the user;

a motion signal detecting device for detecting a motion signal of the user while the user is exercising, the motion signal being transmitted to the audio signal generating device under control of the loop selection controlling signal of the timer control circuit; and, a signal loop selecting circuit having a first signal loop and a second signal loop selectable by the loop selection controlling signal of the timer control circuit, the body signal being transmitted to the audio signal generating device via the first signal loop and the motion signal being transmitted to the audio signal generating device via the second signal loop.

2. The portable audio device as claimed in claim 1, wherein the body signal sensing device comprises a wireless heartbeat signal sensing device which comprises:

a heartbeat detector for detecting a series of heartbeat signals of the user; and a heartbeat signal processing circuit for receiving and processing the heartbeat signals transmitted from the heartbeat detector, and forwarding the heartbeat signals to the audio signal generating device under control of the loop selection controlling signal of the timer control circuit.

3. The portable audio device as claimed in claim 1, wherein the motion signal detecting device comprises a pedometer which includes a pace detector for detecting a pace signal of the user.

4. The portable audio device as claimed in claim 1, wherein the micro-processor further generates an audio control signal to the audio signal generating device to pause the transmission of the audio signal from the audio signal generating device to the audio signal output device during the body signal of the body signal sensing device is transmitted to the audio signal output device.

* * * * *